US 6,582,687 B1

(12) United States Patent
Hamano et al.

(10) Patent No.: US 6,582,687 B1
(45) Date of Patent: Jun. 24, 2003

(54) WEAK ACID SKIN CLEANSER

(75) Inventors: Yohei Hamano, Yokohama (JP);
Toshikatsu Hayashi, Yokahama (JP);
Shin Nakamura, Yokahama (JP);
Yumiko Fujiwara, Yokohama (JP);
Tomiyuki Namba, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/438,981

(22) Filed: Nov. 12, 1999

(30) Foreign Application Priority Data

| Nov. 13, 1998 | (JP) | 10-323318 |
| Nov. 13, 1998 | (JP) | 10-323319 |
| Nov. 13, 1998 | (JP) | 10-323320 |
| Jul. 8, 1999 | (JP) | 11-194412 |

(51) Int. Cl.$^7$ .......................... A61K 31/74; A61K 6/00; A61K 7/00
(52) U.S. Cl. .................. 424/78.03; 424/401; 424/78.02
(58) Field of Search ............... 424/401, 70.19, 424/70.21, 70.22, 78.03, 78.02

(56) References Cited

U.S. PATENT DOCUMENTS

| 4,606,914 | A | * | 8/1986 | Miyoshi | 424/63 |
| 4,673,525 | A | * | 6/1987 | Small et al. | 252/132 |
| 4,992,262 | A | * | 2/1991 | Nakagaki et al. | 424/63 |
| 5,206,012 | A | | 4/1993 | Farer et al. | 424/69 |
| 5,340,492 | A | * | 8/1994 | Kacher et al. | 252/112 |
| 5,529,712 | A | * | 6/1996 | Sano et al. | 252/108 |
| 5,632,978 | A | | 5/1997 | Moore et al. | 510/159 |
| 5,753,242 | A | * | 5/1998 | Nakamura et al. | 424/401 |
| 5,908,617 | A | * | 6/1999 | Moore et al. | 424/70.19 |

FOREIGN PATENT DOCUMENTS

| EP | 0155737 A | 3/1985 |
| EP | 0648833 A | 3/1994 |
| WO | WO9405256 A | 3/1994 |
| WO | WO9617592 A | 6/1996 |
| WO | WO9625144 A | 8/1996 |

OTHER PUBLICATIONS

JP Abstract 04154710. May 27, 1992.*
JP Abstract 04124114. Apr. 24, 1992.*
JP Abstract 407100366. Apr. 18, 1995.*
JP Abstract 07100455. Oct. 15, 1996.*
Patent Abstracts of Japan of JP 08 060182 A (KAO Corp.); 8/94.
Patent Abstracts of Japan of JP 04 154716 A (Shiseido Co., Ltd.); 10/90.
Database WPI, XP002130578 of JP 04 154710 A (Shiseido Co., Ltd.); 10/90.
English Abstract of JP 11–199437; 8/96.
English Abstract of JP 10–219285; 8/98.
English Abstract of JP 10–245590; 9/98.
English Abstract of JP 8507824; 9/94.
English Abstract of JP 8–508753; 10/02.
English Abstract of JP 11–035979; 2/99.
Database WPI, XP002138196 & JP 09 316486 A (Shiseido Co., Ltd.); 3/93.
Morimoto, T., et al. & JP 61 252299 (Mitsui Petrochemical Ind., Ltd. Japan) 11/86.
Kashimoto, A., et al. & JP 05 058842 A (KAO Corp. Japan); 3/93.
Patent Abstracts of Japan & JP 10 23498 A (Kose Corp); 9/98.
Patent Abstracts of Japan of JP 54 050513 A (Kanebo, Ltd.) 4/79.
Patent Abstracts of Japan of JP 62 234015 A (Lion Corp.); 10/87.
Patent Abstracts of Japan of JP 08 269493 A (Shiseido Co., Ltd.); 10/96.
Patent Abstracts of Japan of JP 08 060189 A (Ajinomoto Co., Inc); 5/96.
Patent Abstracts of Japan of JP 08 060182 A (KAO Corp.); 3/96.
Patent Abstracts of Japan of JP 04 154716 A (Shiseido Co., Ltd.); 3/92.
Database WPI, XP002130578 of JP 04 154710 A (Shiseido Co., Ltd); 5/92.
Patent Abstracts of Japan of JP 54 050513 A (Kanebo, Ltd.); 4/79.
Patent Abstracts of Japan of JP 62 234015 A (Lion Corp.); 10/87.
Patent Abstracts of Japan of JP 08 269493 A (Shiseido Co., Ltd.); 10/96.
Patent Abstracts of Japan of JP 08 060189 A (Ajinomoto Co., Inc.); 3/96.

* cited by examiner

Primary Examiner—Russell Travers
Assistant Examiner—Lauren Q. Wells
(74) Attorney, Agent, or Firm—Townsend & Banta

(57) ABSTRACT

A weak acid skin cleanser containing an alkali salt of N-acylamino acid and maltitolhydroxy aliphatic ether, or a hydroxy ether carboxylic acid-based anionic surfactant, or polyethylene powder, as well as water and an organic acid. Also, a weak acid skin cleanser containing an alkali salt of N-acylamino acid, a betaine-based ampholytic surfactant, water, and an organic acid. The weak acid skin cleansers mentioned above provide creamy and rich foaming, rapid rinsing, refreshing sensation during use, moist skin sensation after cleaning, and shelf stability of the base agent (separation, offensive odor, discoloration, etc.), and are free of increasing hardness over time at room temperature and below.

4 Claims, 1 Drawing Sheet

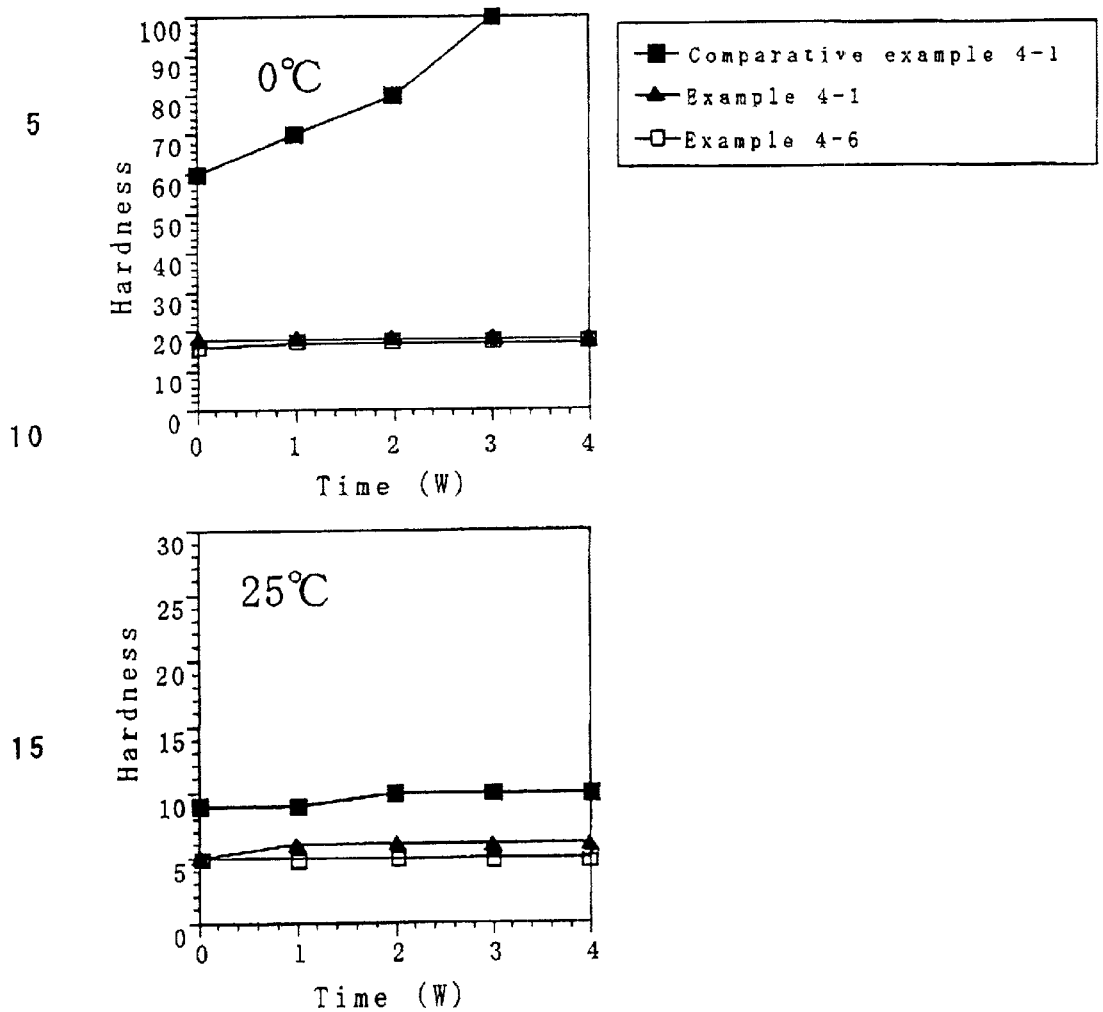
FIG. 1 The change in the hardness of each example over time

WEAK ACID SKIN CLEANSER

RELATED APPLICATION

This application claims the priority of Japanese Patent applications No.10-323318, No. 10-323319 and No. 10-323320 filed on Nov. 13, 1998, and No. 11-194412 filed on Jul. 8, 1999, which are incorporated herein by reference.

BACKGROUND OF THE INVENTION

1. Field of the invention

This invention relates in general to a skin cleanser, and more particularly to a weak acid skin cleanser which has creamy and rich foaming, rapid rinsing, and a moist skin sensation after cleaning when used for skin cleaning for the purpose of cleaning off skin stains and sebum.

2. The Prior Art

Conventionally, soap, which is an alkali salt of a fatty acid, has been used as the base cleanser of a cleanser for the purpose of washing skin.

It is well known that soap has a superior cleaning effect and is superior in terms of giving agreeable sensations during skin cleaning such as creamy and rich foaming, rapid rinsing, and a refreshing sensation, and therefore is used as cleansing foam, bath soap, and face washing soap in many skin cleaning applications.

However, on the other hand, the refreshing sensation of soap is so strong that a moist and agreeable sensation after cleaning is hard to obtain. Despite blending in various oil components and/or synthetic surfactants in a cleanser or adjustments in the recipe by changing the soap content and such, a moist skin sensation after cleaning cannot be obtained in practical use.

Also, a feature demanded by consumers for a skin cleanser is to have weak acidity which is close to skin pH. However, recipes whose main ingredient is soap, which is intrinsically highly alkaline, cannot respond to such a demand.

For the purpose of obtaining a weak acid skin cleanser which has a superior cleaning effect, gives agreeable sensations during skin washing such as creamy and rich foaming, rapid rinsing, and a refreshing sensation, as well as a superior moist skin sensation after cleaning, and thus responds to consumers' demand, base cleansers other than soap including alkali salts of acylglutamic acid, alkali salts of acylsarcosinic acid, alkali salts of alkylsulfosuccinic acid, and alkali salts of alkylphosphoric acid have been used.

The Invention of Claims 1–9

However, they have problems with at least one item in the group of items that includes the cleaning effect, creamy and rich foaming, rapid rinsing, refreshing sensation during use, moist skin sensation after cleaning, and shelf stability of the base agent (separation, offensive odor, discoloration, etc.). It has been very difficult to obtain a weak acid cleanser which is satisfactory in all these aspects.

In view of the aforementioned problem, the inventors conducted earnest research to develop a weak acid cleanser which has a satisfactory effect in terms of all these items, which include the cleaning effect, creamy and rich foaming, rapid rinsing, refreshing sensation during use, moist skin sensation after cleaning, and shelf stability of the base agent (separation, offensive odor, discoloration, etc.). As a result, we discovered that a weak acid skin cleanser which contains alkali salt of N-acylamino acid and maltitolhydroxy aliphatic ether, or a hydroxy ether carboxylic acid-based anionic surfactant, or polyethylene powder can beautifully solve the aforementioned problem, thus completing the present invention.

The object of the present invention is to develop a new weak acid skin cleanser which is superior in terms of the cleaning effect, creamy and rich foaming, rapid rinsing, refreshing sensation during use, moist skin sensation after cleaning, and shelf stability of the base agent (separation, offensive odor, discoloration, etc.) and thus responds to consumers' demand.

The Invention of Claims 10–13

However, when the aforementioned cleanser base agent was used to prepare a skin cleanser in a paste form, there was a fatal problem in that the hardness increased over time at room temperature or lower temperatures and therefore the skin cleanser became hard to squeeze out of a tube.

In view of the aforementioned problem, the inventors conducted earnest research to develop a cleanser which does not have a problem in that the hardness increases over time at room temperature or lower temperatures and therefore the skin cleanser becomes hard to squeeze out of a tube. As a result, we discovered that a weak acid skin cleanser which contains alkali salt of N-acylamino acid and a betaine-based ampholytic surfactant can beautifully solve the aforementioned problem, thus completing the present invention.

The object of the present invention is to develop a weak acid skin cleanser which solves the problem of the conventional technology, i.e. the hardness increases over time at room temperature or lower temperatures and therefore the skin cleanser becomes hard to squeeze out of a tube.

BRIEF SUMMARY OF THE INVENTION

The Invention of Claims 1–9

That is, the present invention provides a weak acid skin cleanser which characteristically contains alkali salt of N-acylamino acid, maltitolhydroxy aliphatic ether, water, and organic acid.

Also, the present invention provides a weak acid skin cleanser which characteristically contains alkali salt of N-acylamino acid, a hydroxy alkyl ether carboxylic acid-based anionic surfactant, water, and organic acid.

Furthermore, the present invention provides a weak acid skin cleanser which characteristically contains alkali salt of N-acylamino acid, polyethylene powder, water, and organic acid.

Also, the present invention provides the aforementioned weak acid skin cleanser wherein said alkali salt of N-acylamino acid is N-acylglycine salt.

Furthermore, the present invention provides the aforementioned weak acid skin cleanser wherein the content of said alkali salt of N-acylamino acid is 1–5.0 wt % of the total amount of the weak acid skin cleanser.

Also, the present invention provides the aforementioned weak acid skin cleanser wherein the content of said maltitolhydroxy aliphatic ether is 0.01–5 wt % of the total amount of the weak acid skin cleanser.

Furthermore, the present invention provides the aforementioned weak acid skin cleanser wherein the content of hydroxy alkyl ether carboxylic acid-based anionic surfactant is 0.1–20 wt % of the total amount of the weak acid skin cleanser.

Also, the present invention provides the aforementioned weak acid skin cleanser wherein the content of said polyethylene powder is 0.5–5 wt % of the total amount of the weak acid skin cleanser.

Furthermore, the present invention provides the aforementioned weak acid skin cleanser additionally containing a water soluble compound with a hydroxyl group.

The Invention of Claims 10–13

That is, the present invention provides a weak acid skin cleanser which characteristically contains alkali salt of N-acylamino acid, a betaine-based ampholytic surfactant, water, and organic acid.

Also, the present invention provides the aforementioned weak acid skin cleanser wherein said alkali salt of N-acylamino acid is N-acylglycine salt.

Furthermore, the present invention provides the aforementioned weak acid skin cleanser wherein said betaine-based ampholytic surfactant is one or more compounds represented by the following chemical formulas (1), (2), (3), or (4).

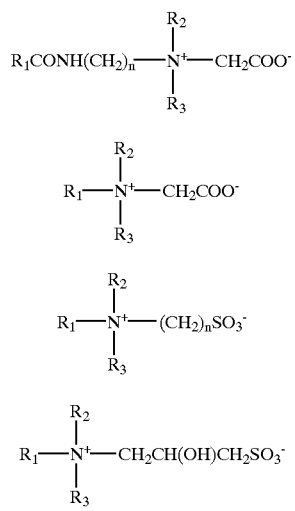

(In this formula, $R_1$ denotes an alkyl group or alkenyl group with a carbon number of 8–21, $R_2$ and $R_3$ denotes alkyl groups with a carbon number of 1–3, and n denotes an integer 1–4.)

Also, the present invention provides the aforementioned weak acid skin cleanser which is in a paste form wherein the content of the alkali salt of N-acylamino acid is 5–50 wt % and the content of the betaine-based ampholytic surfactant is 0.1–30 wt % of the total amount of the weak acid skin cleanser.

BRIEF DESCRIPTION OF THE DRAWINGS

The Invention of Claims 10–13

FIG. 1 shows the change in the hardness of Examples and Comparative examples over time at 0° C. and 25° C.

DETAILED DESCRIPTION OF THE INVENTION

The Invention of Claims 1–9

The configuration of the present invention is described in detail below.

The alkali salt of N-acylamino acid used in the present invention is a prior art N-acylamino acid-based surfactant. In the present invention it is a surfactant which gives superior stability, has good affinity with stains, gives a refreshing sensation during rinsing, is easy to rinse off, and gives a moist skin sensation after use.

The carbon number of the acylated portion of the N-acylamino acid (RCO—) is 10–18, preferably 12–14. If the carbon number is less than 1.0, then the viscosity of the cleanser is reduced and also foaming is reduced. If the carbon number is more than 18, then the hardness of the cleanser increases and also the foaming is reduced. Either the straight chain or branched chain, and saturated or unsaturated can be used. However, the straight chain is preferable in terms of foaming and the saturated is preferable in terms of stability. Particularly preferable in the present invention is a straight chain acyl group with a carbon number of 12 and a coconut oil fatty acid acyl group which has this group as a main ingredient.

For the amino acid site, glutamic acid, alanine, glycine, etc. are preferable. Considering the pharmaceutical preparation, an N-acylglycine salt is the most preferable.

For the alkali salt, sodium salts, potassium salts, and triethanolamine salts, for example, are preferable. Considering the foaming and the pharmaceutical preparation, sodium salt is the most preferable.

The most preferable alkali salt of N-acylamino acid is sodium acyl glycinate.

The sodium acyl glycinate used in the present invention is a prior art amino acid-based surfactant with the following structure, derived from glycine, which is a main component in human skin collagen, and a fatty acid such as coconut fatty acid.

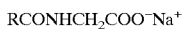 [Chemical Formula 1]

(R denotes a straight chain or branched chain, saturated or unsaturated hydrocarbon group with a carbon number of 9–17.)

The carbon number of the acyl group (RCO—) is 10–18, preferably 12–14. If the carbon number is less than 10, then the viscosity of the cleanser is reduced and also foaming is reduced. If the carbon number is more than 18, then the hardness of the cleanser increases and also the foaming is reduced. Either the straight chain or branched chain, and saturated or unsaturated can be used. However, the straight chain is preferable in terms of foaming and the saturated is preferable in terms of stability. Particularly preferable in the present invention is a straight chain acyl group with a carbon number of 12 and a coconut oil fatty acid acyl group which has this group as a main ingredient.

In this invention a commercial product which is solid at ordinary temperatures, such as Amilite (registered trademark: from Ajinomoto Co., Ltd.), can be used.

The content of the alkali salt of N-acylamino acid varies depending on the formulation of the skin cleanser product and is 1–20 wt % of the total skin cleanser for liquid products, 5–50 wt % for paste products, and 40–90 wt % for solid products. Considering creamy and rich foaming, rapid foaming, rapid rinsing, and the ease of use, paste products with 10–40 wt % blended in is particularly preferable.

Maltitolhydroxy aliphatic ether used in the present invention is a prior art surfactant, and, in the present invention, it is particularly effective for improving the foaming and making the foam distinctively creamy. The carbon number of the maltitolhydroxy aliphatic ether is 6–22, preferably 12–18. Specific examples include maltitol-2-hydroxy myristyl ether, maltitol-2-hydroxy lauryl ether, and maltitol-2-hydroxy stearyl ether.

The content of maltitolhydroxy aliphatic ether is typically 0.01–5 wt %, preferably 0.1–2 wt %, of the total amount of the weak acid skin cleanser.

The hydroxy ether carboxylic acid-based anionic surfactant used in the present invention is a prior art surfactant, and, in the present invention, it is particularly effective for improving the foaming and making the foam distinctively creamy. The carbon number of the hydroxy ether carboxylic acid-based anionic surfactant is 6–22, preferably 12–18. Specific examples include sodium salt of hydroxy ether aliphatic acid, potassium salt of hydroxy ether aliphatic acid, and triethanolamine salt of hydroxy ether aliphatic acid. Sodium salt of hydroxy ether aliphatic acid is particularly preferable. Specifically, sodium dodecane-1,2-diol acetic ether is preferable.

The content of the hydroxy ether carboxylic acid-based anionic surfactant is typically 0.1–20 wt %, preferably 2–10 wt %, of the total amount of the weak acid skin cleanser.

The selection of polyethylene powder used in the present invention is not limited in particular as long as it is powder for use in cosmetics. The average particle size is preferably 1–50 micrometers. In the present invention, it is particularly effective for improving the foaming and making the foam distinctively creamy.

The content of polyethylene powder is typically 0.5–5 wt %, preferably 1–2 wt %, of the total amount of the weak acid skin cleanser.

The betaine-based ampholytic surfactant used in the present invention is a prior art surfactant represented by the aforementioned chemical formulas (1), (2), (3), or (4). Specific examples include N-alkyl-N-carboxymethyl ammonium betaine, 2-alkyl-1-hydroxyethyl imidazolium betaine sodium salt, alkyldimethyl aminoacetic acid betaine, alkylimidazolinium betaine, cocoyl amido propyldimethyl glycine, coconut oil alkyl betaine, lauryldimethylamino-2-hydroxypropylsulfo betaine, lauric acid amide propyl betaine, and lauryldimethylaminopropylsulfo betaine. These surfactants can be used independently or in combinations of two or more.

In the present invention, the betaine-based ampholytic surfactant suppresses the increase in the hardness of a paste cleanser having a N-acylamino acid-based surfactant as the main agent at room temperature or lower temperatures so as to improve the ease of squeezing it out of a tube, and also improves the rapid lathering.

The content of the betaine-based ampholytic surfactant is 0.1–30 wt % of the total skin cleanser. When the content is less than 0.1 wt %, then the effect is not sufficient. Blending in more than 30 wt % would not improve the effect and is disadvantageous in terms of cost; safety and stability can be a problem as well. Considering the effect of suppressing the increase in the hardness and the ease of use, paste products with 0.5–15 wt % blended in is particularly preferable.

In the present invention, in addition to the aforementioned essential ingredients, it is preferable to blend in one or more water soluble compounds having a hydroxyl group chosen from the group consisting of lower alcohols, polyhydric alcohols, ethylene glycol adducts of polyhydric alcohol, and propylene oxide adducts of polyhydric alcohol. Specific examples include ethyl alcohol, isopropyl alcohol, butanol, propylene glycol, isopropylene glycol, 1,3 butanediol, dipropylene glycol, glycerine, diglycerine, polyglycerine, trimethylol propane, erythritol, pentaerythritol, sorbitan, sorbitol glucose, maltitol, saccharose, trehalose, and fructose, as well as their derivatives such as ethylene oxide adducts and propylene oxide adducts. In terms of sufficiently satisfying all the items, i.e. cleaning effect, creamy and rich foaming, rapid rinsing, refreshing sensation during use, moist skin sensation after cleaning, and stability of the base agent, glycerine or 1,3 butanediol is most preferably used.

The content of the water soluble compound having a hydroxyl group is preferably 1–40 wt %, more preferably 5–20 wt %, of the total amount of the weak acid skin cleanser.

Also, some oil component can be blended into the weak acid skin cleanser of the present invention. When oil components are blended in, the sensation during use, such as refreshing sensation, decreases somewhat, but the moist skin sensation after cleansing is augmented. The oil component mentioned here refers to, for example, hydrocarbons, higher alcohols, higher fatty acids, higher alcohol higher fatty acid esters, animal and plant oils/fats, cholesterol fatty acid esters, and silicones. Specific examples include liquid petrolatum, polyisobutene, isostearylcholesteryl ester, 2-ethylhexylic acid triglyceride, hexadecyl 2-ethylhexanoate, octadecyl myristate, olive oil, chain or ring methyl polysiloxane, etc.

In addition to the aforementioned ingredients, the weak acid skin cleanser of the present invention contains water and organic acid such as citric acid to make the pH weakly acidic. The content of water and the organic acid is determined according to the formulation of the skin cleanser.

The skin cleanser of the present invention is prepared with a conventional method according to the target formulation after adding, as necessary, other ingredients which are usually blended in a skin cleanser, such as a thickener, ionic surfactant, active ingredient, humectant, anti-inflammatory, disinfectant, preservative, ultraviolet light absorbent, antioxidant, organic and inorganic powder, pigment, and perfume.

The Invention of Claims 1–9

According to the present invention, a weak acid cleanser can be provided which has satisfactory effects in terms of all the following items: the skin cleaning effect, creamy and rich foaming, rapid rinsing, refreshing sensation during use, moist skin sensation after cleaning, and shelf stability of the base agent (separation, offensive odor, discoloration, etc.).

The Invention of Claims 10–13

According to the present invention, a weak acid cleanser can be provided which is free of increasing hardness over time at room temperature and lower temperatures, (when used as paste to fill a tube) solves the fatal problem of becoming difficult to squeeze out of a tube after allowing to stand at room temperature and lower temperatures, and gives rapid lathering, creamy and rich foaming, rapid rinsing, a refreshing sensation during skin cleaning, and a moist sensation after cleaning.

EXAMPLES

The present invention is described in detail by referring to examples below. The present invention is not limited to these examples. The blend ratios in examples are indicated in weight percent units.

The Invention of Claims 1–9

Evaluation Method and Evaluation Criteria for Sensation During Use

A panel of 18 healthy women (20–45 years old), after their skin was washed with water and dried, had 0.5 g of petrolatum homogeneously applied on their faces. Thirty minutes later, the skin cleansers of Examples and Comparative examples were used to wash their faces. Foaming, ease of rinsing, refreshing sensation during use and moist sensation after face washing were evaluated. For each evaluation, the top number of evaluation points was 100. Evaluation was based on the following criteria by using the average points of the 18 women. The results are shown in Tables 1–6.

"① Foaming"

⊚: Evaluation points of 75 or higher (Very good foaming)

○: Evaluation points of 50–75 (Good foaming)

Δ: Evaluation points of 25–50 (Somewhat poor foaming)

X: Evaluation points of 25 or lower (Poor foaming)

"② Creamy Foam"

⊚: Evaluation points of 75 or higher (Very creamy)

○: Evaluation points of 50–75 (Creamy)

Δ: Evaluation points of 25–50 (Not very creamy)

X: Evaluation points of 25 or lower (Not creamy at all)

"③ Easy Rinsing"

⊚: Evaluation points of 75 or higher (Very easy to rinse)

○: Evaluation points of 50–75 (Easy to rinse)

Δ: Evaluation points of 25 or lower (Fairly hard to rinse)

X: Evaluation points of 25 or lower (Fairly hard to rinse)

"④ Refreshing Sensation During Use"

⊚: Evaluation points of 75 or higher (Very refreshing)

○: Evaluation points of 50–75 (Refreshing)

Δ: Evaluation points of 25–50 (Some residue is sensed.)

X: Evaluation points of 25 or lower (Residue is sensed.)

"⑤ Moist Sensation After Face Washing"

⊚: Evaluation points of 75 or higher (Very moist)

○: Evaluation points of 50–75 (Moist)

Δ: Evaluation points of 25–50 (Not very moist)

X: Evaluation points of 25 or lower (Not moist at all)

"Evaluation Method and Evaluation Criteria for Stability"

Glass bottles (with lids) were 90% filled with the skin cleansers of Examples and Comparative examples. They were allowed to stand in a thermo-hygrostat with a temperature of 40° C. and a relative humidity of 75% and observed for days. After four weeks, the evaluation was conducted according to the following evaluation criteria. The results are shown in Tables 1–6.

⊚: Even after four weeks, no change in the state was observed in terms of separation, offensive odor, or discoloration.

○: Even after four weeks, almost no change in the state was observed in terms of separation, offensive odor, or discoloration.

Δ: After four weeks, some changes in the state were observed in terms of separation, offensive odor, and/or discoloration.

X: After four weeks, distinctive changes in the state were observed in terms of separation, offensive odor, and/or discoloration.

1: Examples of the invention of Claim 1

<Example 1-1> Liquid cleanser

| | |
|---|---|
| Sodium acyl glycinate | 25 wt % |
| Maltitolhydroxy aliphatic ether | 0.1 |
| Glycerine | 5 |
| Propylene glycol | 5 |
| Thickener | Appropriate amount |
| Citric acid | Appropriate amount |
| Preservative | Appropriate amount |
| Water | Balance |

<Comparative example 1-1> Liquid cleanser

| | |
|---|---|
| Sodium acyl saracosinate | 25 wt % |
| Glycerine | 5 |
| Propylene glycol | 5 |
| Thickener | Appropriate amount |
| Citric acid | Appropriate amount |
| Preservative | Appropriate amount |
| Water | Balance |

<Example 1-2> Paste cleanser

| | |
|---|---|
| Sodium acyl glycinate | 30 wt % |
| Maltitolhydroxy aliphatic ether | 0.5 |
| Glycerine | 30 |
| Propylene glycol | 5 |
| Polyethylene glycol (Average molecular weight: 20,000) | 1 |
| Citric acid | Appropriate amount |
| Water | Balance |

<Comparative example 1-2> Paste cleanser

| | |
|---|---|
| Sodium acyl glutamate | 30 wt % |
| Glycerine | 30 |
| Propylene glycol | 5 |
| Polyethylene glycol (Average molecular weight: 20,000) | 1 |
| Citric acid | Appropriate amount |
| Water | Balance |

<Example 1-3> Solid cleanser

| | |
|---|---|
| Sodium acyl glycinate | 85 wt % |
| Maltitolhydroxy aliphatic ether | 1 |
| Glycerine | 5 |
| Citric acid | Appropriate amount |
| Preservative | Appropriate amount |
| Water | Balance |

<Comparative example 1-3> Solid cleanser

| | |
|---|---|
| Sodium alkylsufosuccinate | 85 wt % |
| Glycerine | 5 |
| Citric acid | Appropriate amount |
| Preservative | Appropriate amount |
| Water | Balance |

Preparation Method

The aforementioned ingredients are homogeneously mixed with a high speed mixer under heated conditions of 60° C.–80° C. After defoaming, filtration, and cooling, a weak acid skin cleanser is obtained.

TABLE 1

| Evaluation item | Example 1-1 | Comparative example 1-1 | Example 1-2 | Comparative example 1-2 | Example 1-3 | Comparative example 1-3 |
|---|---|---|---|---|---|---|
| ① | ◎ | △ | ◎ | △ | ◎ | ○ |
| ② | ◎ | △ | ◎ | △ | ◎ | ○ |
| ③ | ◎ | ○ | ◎ | ◎ | ◎ | △ |
| ④ | ◎ | ◎ | ◎ | ◎ | ◎ | △ |
| ⑤ | ○ | △ | ◎ | ◎ | ○ | ○ |
| Stability | ○ | ○ | ◎ | △ | ○ | △ |

Comparative example 1-1 not only has a problem in the foaming of sodium acyl sarcosinate in the weakly acidic area, but also lacks creaminess of the foam and gives an insufficient moist sensation after face washing. However, Example 1-1 solves or improves these issues. Comparative example 1-2 gives a relatively good weak acid skin cleanser except for the fact that the foaming of sodium acyl glutamate is not sufficient, the foam is not creamy, and the paste tends to become hard. However, Example 1-2 achieves even better evaluation. As for Comparative 1-3, alkylsulfosuccinic acid gives a relatively non-refreshing sensation during use. Example 1-3 is superior to Comparative example 1-3 in terms of easy rinsing and refreshing sensation during use.

Other examples are listed below.

<Example 1-4> Liquid cleanser

| | |
|---|---|
| Potassium acyl glycinate | 25 wt % |
| Maltitolhydroxy aliphatic ether | 0.1 |
| Glycerine | 5 |
| Propylene glycol | 5 |
| Thickener | Appropriate amount |
| Citric acid | Appropriate amount |
| Preservative | Appropriate amount |
| Water | Balance |

<Example 1-5> Paste cleanser

| | |
|---|---|
| Potassium acyl glutamate | 30 wt % |
| Maltitolhydroxy aliphatic ether | 0.5 |
| Glycerine | 30 |
| Propylene glycol | 5 |
| Polyethylene glycol (Average molecular weight: 20,000) | 1 |
| Citric acid | Appropriate amount |
| Water | Balance |

<Example 1-6> Solid cleanser

| | |
|---|---|
| Sodium salt of acyl alanine | 85 wt % |
| Maltitolhydroxy aliphatic ether | 1 |
| Glycerine | 5 |
| Citric acid | Appropriate amount |
| Preservative | Appropriate amount |
| Water | Balance |

TABLE 2

| Evaluation item | Example 1-4 | Example 1-5 | Example 1-6 |
|---|---|---|---|
| ① | ○ | ○ | ○ |
| ② | ○ | ○ | ○ |
| ③ | ◎ | ◎ | ◎ |
| ④ | ◎ | ◎ | ◎ |
| ⑤ | ○ | ◎ | ○ |
| Stability | ○ | ○ | ○ |

2: Examples of the invention of Claim 2

<Example 2-1> Liquid cleanser

| | |
|---|---|
| Sodium acyl glycinate | 10 wt % |
| Sodium salt of hydroxyalkyl ether fatty acid | 15 |
| Glycerine | 5 |
| Propylene glycol | 5 |
| Citric acid | Appropriate amount |
| Water | Balance |

<Comparative example 2-1> Liquid cleanser

| | |
|---|---|
| Sodium acyl saracosinate | 25 wt % |
| Glycerine | 5 |
| Propylene glycol | 5 |
| Citric acid | Appropriate amount |
| Water | Balance |

<Example 2-2> Paste cleanser

| | |
|---|---|
| Sodium acyl glycinate | 20 wt % |
| Sodium salt of hydroxyalkyl ether fatty acid | 5 |
| Glycerine | 30 |
| Propylene glycol | 5 |
| Polyethylene glycol (Average molecular weight: 20,000) | 1 |
| Citric acid | Appropriate amount |
| Water | Balance |

<Comparative example 2-2> Paste cleanser

| | |
|---|---|
| Sodium acyl glutamate | 30 wt % |
| Glycerine | 30 |
| Propylene glycol | 5 |
| Polyethylene glycol (Average molecular weight: 20,000) | 1 |
| Citric acid | Appropriate amount |
| Water | Balance |

<Example 2-3> Solid cleanser

| | |
|---|---|
| Sodium acyl glycinate | 85 wt % |
| Sodium salt of hydroxyalkyl ether fatty acid | 1 |
| Glycerine | 5 |
| Citric acid | Appropriate amount |
| Water | Balance |

<Comparative example 2-3> Solid cleanser

| | |
|---|---|
| Sodium alkylsufosuccinate | 85 wt % |
| Glycerine | 5 |
| Citric acid | Appropriate amount |
| Water | Balance |

Preparation Method

The aforementioned ingredients are homogeneously mixed with a high speed mixer under heated conditions of 60° C.–80° C. After defoaming, filtration, and cooling, a weak acid skin cleanser is obtained.

TABLE 3

| Evaluation item | Example 2-1 | Comparative example 2-1 | Example 2-2 | Comparative example 2-2 | Example 2-3 | Comparative example 2-3 |
|---|---|---|---|---|---|---|
| ① | ◎ | △ | ◎ | △ | ◎ | ○ |
| ② | ◎ | △ | ◎ | △ | ◎ | ○ |
| ③ | ◎ | ○ | ◎ | ◎ | ◎ | △ |
| ④ | ◎ | ◎ | ◎ | ◎ | ◎ | △ |
| ⑤ | ○ | △ | ◎ | ◎ | ○ | ○ |
| Stability | ○ | ○ | ◎ | △ | ○ | △ |

Comparative example 2-1 not only has a problem in the foaming of sodium acyl sarcosinate in the weakly acidic area, but also lacks creaminess of the foam and gives an insufficient moist sensation after face washing. However, Example 2-1 solves or improves these issues. Comparative example 2-2 gives a relatively good weak acid skin cleanser except for the fact that the foaming of sodium acyl glutamate is not sufficient, the foam is not creamy, and the paste tends to become hard. However, Example 2-2 achieves even better evaluation. As for Comparative 2-3, alkylsulfosuccinic acid gives a relatively non-refreshing sensation during use. Example 2-3 is superior to Comparative example 2-3 in terms of easy rinsing and refreshing sensation during use.

Other examples are listed below.

<Example 2-4> Liquid cleanser

| | |
|---|---|
| Potassium acyl glutamate | 10 wt % |
| Sodium salt of hydroxyalkyl ether fatty acid | 15 |
| Glycerine | 5 |
| Propylene glycol | 5 |
| Citric acid | Appropriate amount |
| Water | Balance |

<Example 2-5> Paste cleanser

| | |
|---|---|
| Potassium acyl glycinate | 20 wt % |
| Triethanolamine salt of hydroxyalkyl ether fatty acid | 5 |
| Glycerine | 30 |
| Propylene glycol | 5 |
| Polyethylene glycol (Average molecular weight: 20,000) | 1 |
| Citric acid | Appropriate amount |
| Water | Balance |

<Example 2-6> Solid cleanser

| | |
|---|---|
| Sodium salt of acyl alanine | 85 wt % |
| Potassium salt of hydroxyalkyl ether fatty acid | 1 |
| Glycerine | 5 |
| Citric acid | Appropriate amount |
| Water | Balance |

TABLE 4

| Evaluation item | Example 2-4 | Example 2-5 | Example 2-6 |
|---|---|---|---|
| ① | ○ | ○ | ◎ |
| ② | ◎ | ◎ | ◎ |
| ③ | ◎ | ◎ | ◎ |
| ④ | ◎ | ◎ | ◎ |
| ⑤ | ◎ | ○ | ○ |
| Stability | ○ | ○ | ○ |

3: Examples of the invention of Claim 3

<Example 3-1> Liquid cleanser

| | |
|---|---|
| Sodium acyl glycinate | 25 wt % |
| Polyethylene powder | 0.1 |
| Glycerine | 5 |
| Propylene glycol | 5 |
| Thickener | Appropriate amount |
| Citric acid | Appropriate amount |
| Preservative | Appropriate amount |
| Water | Balance |

<Comparative example 3-1> Liquid cleanser

| | |
|---|---|
| Sodium acyl saracosinate | 25 wt % |
| Glycerine | 5 |
| Propylene glycol | 5 |
| Thickener | Appropriate amount |
| Citric acid | Appropriate amount |
| Preservative | Appropriate amount |
| Water | Balance |

<Example 3-2> Paste cleanser

| | |
|---|---|
| Sodium acyl glycinate | 30 wt % |
| Polyethylene powder | 2 |
| Glycerine | 30 |
| Propylene glycol | 5 |
| Polyethylene glycol (Average molecular weight: 20,000) | 1 |
| Citric acid | Appropriate amount |
| Water | Balance |

<Comparative example 3-2> Paste cleanser

| | |
|---|---|
| Sodium acyl glutamate | 30 wt % |
| Glycerine | 30 |
| Propylene glycol | 5 |
| Polyethylene glycol (Average molecular weight: 20,000) | 1 |
| Citric acid | Appropriate amount |
| Water | Balance |

<Example 3-3> Solid cleanser

| | |
|---|---|
| Sodium acyl glycinate | 85 wt % |
| Polyethylene powder | 5 |
| Glycerine | 5 |
| Citric acid | Appropriate amount |
| Preservative | Appropriate amount |
| Water | Balance |

<Comparative example 3-3> Solid cleanser

| | |
|---|---|
| Sodium alkylsufosuccinate | 85 wt % |
| Glycerine | 5 |
| Citric acid | Appropriate amount |
| Preservative | Appropriate amount |
| Water | Balance |

Preparation Method

The aforementioned ingredients are homogeneously mixed with a high speed mixer under heated conditions of 60° C.–80° C. After defoaming, filtration, and cooling, a weak acid skin cleanser is obtained.

TABLE 5

| Evaluation item | Example 3-1 | Comparative example 3-1 | Example 3-2 | Comparative example 3-2 | Example 3-3 | Comparative example 3-3 |
|---|---|---|---|---|---|---|
| ① | ◎ | △ | ◎ | △ | ◎ | ○ |
| ② | ◎ | △ | ◎ | △ | ◎ | ○ |
| ③ | ◎ | ○ | ◎ | ◎ | ◎ | △ |
| ④ | ◎ | ◎ | ◎ | ◎ | ◎ | △ |
| ⑤ | ○ | △ | ◎ | ◎ | ○ | ○ |
| Stability | ○ | ○ | ◎ | △ | ○ | △ |

Comparative example 3-1 not only has a problem in the foaming of sodium acyl sarcosinate in the weakly acidic area, but also lacks creaminess of the foam and gives an insufficient moist sensation after face washing. However, Example 3-1 solves or improves these issues. Comparative example 3-2 gives a relatively good weak acid skin cleanser except for the fact that the foaming of sodium acyl glutamate is not sufficient, the foam is not creamy, and the paste tends to become hard. However, Example 3-2 achieves even better evaluation. As for Comparative 3-3, alkylsulfosuccinic acid gives a relatively non-refreshing sensation during use. Example 3-3 is superior to Comparative example 3-3 in terms of easy rinsing and refreshing sensation during use.

Other examples are listed below.

<Example 3-4> Liquid cleanser

| | |
|---|---|
| Potassium acyl glycinate | 25 wt % |
| Polyethylene powder | 0.1 |
| Glycerine | 5 |
| Propylene glycol | 5 |
| Thickener | Appropriate amount |
| Citric acid | Appropriate amount |
| Preservative | Appropriate amount |
| Water | Balance |

<Example 3-5> Paste cleanser

| | |
|---|---|
| Sodium acyl glutamate | 30 wt % |
| Polyethylene powder | 2 |
| Glycerine | 30 |
| Propylene glycol | 5 |
| Polyethylene glycol (Average molecular weight: 20,000) | 1 |
| Citric acid | Appropriate amount |
| Water | Balance |

<Example 3-6> Solid cleanser

| | |
|---|---|
| Sodium salt of acyl alanine | 85 wt % |
| Polyethylene powder | 5 |
| Glycerine | 5 |
| Citric acid | Appropriate amount |
| Preservative | Appropriate amount |
| Water | Balance |

TABLE 6

| Evaluation item | Example 3-4 | Example 3-5 | Example 3-6 |
|---|---|---|---|
| ① | ○ | ○ | ◎ |
| ② | ◎ | ○ | ◎ |
| ③ | ◎ | ◎ | ◎ |
| ④ | ◎ | ◎ | ◎ |
| ⑤ | ○ | ◎ | ○ |
| Stability | ○ | ○ | ○ |

The Invention of Claims 10–13

<Example 4-1> Paste cleanser

| | |
|---|---|
| Sodium N-acyl glycinate | 20 |
| Cocoyl amido propyldimethyl glycine | 2 |
| Glycerine | 30 |
| Propylene glycol | 5 |
| Thickener | Appropriate amount |
| Citric acid | Appropriate amount |
| Preservative | Appropriate amount |
| Water | Balance |

<Comparative example 4-1> Paste cleanser

| | |
|---|---|
| Sodium N-acyl glycinate | 20 |
| Glycerine | 30 |
| Propylene glycol | 5 |
| Thickener | Appropriate amount |
| Citric acid | Appropriate amount |
| Preservative | Appropriate amount |
| Water | Balance |

<Example 4-2> Paste cleanser

| | |
|---|---|
| Sodium N-acyl glutamate | 30 |
| Cocoyl amido propyldimethyl glycine | 5 |
| Glycerine | 5 |
| Propylene glycol | 5 |
| Polyethylene glycol | 1 |
| Citric acid | Appropriate amount |
| Water | Balance |

<Comparative example 4-2> Paste cleanser

| | |
|---|---|
| Sodium N-acyl glutamate | 30 |
| Glycerine | 5 |
| Propylene glycol | 5 |
| Polyethylene glycol | 1 |
| Citric acid | Appropriate amount |
| Water | Balance |

<Example 4-3> Paste cleanser

| | |
|---|---|
| Sodium salt of N-acyl alanine | 30 |
| Cocoyl amido propyldimethyl glycine | 5 |
| Glycerine | 5 |
| Propylene glycol | 5 |
| Polyethylene glycol | 1 |
| Citric acid | Appropriate amount |
| Water | Balance |

<Comparative example 4-3> Paste cleanser

| | |
|---|---|
| Sodium salt of N-acyl alanine | 30 |
| Glycerine | 5 |
| Propylene glycol | 5 |
| Polyethylene glycol | 1 |
| Citric acid | Appropriate amount |
| Water | Balance |

<Example 4-4> Paste cleanser

| | |
|---|---|
| Sodium N-acyl glycinate | 30 |
| Alkyldimethylaminoacetic acid betaine | 10 |
| Glycerine | 30 |
| Propylene glycol | 5 |

-continued

| | |
|---|---|
| Polyethylene glycol | 1 |
| Citric acid | Appropriate amount |
| Water | Balance |
| <Comparative example 4-4> Paste cleanser | |
| | |
| Sodium N-acyl glycinate | 30 |
| Glycerine | 30 |
| Propylene glycol | 5 |
| Polyethylene glycol | 1 |
| Citric acid | Appropriate amount |
| Water | Balance |
| <Example 4-5> Paste cleanser | |
| | |
| Potassium N-acyl glycinate | 30 |
| Alkylimidazolinium betaine | 3 |
| Glycerine | 30 |
| Propylene glycol | 5 |
| Polyethylene glycol | 1 |
| Citric acid | Appropriate amount |
| Water | Balance |
| <Example 4-6> Paste cleanser | |
| | |
| Sodium N-acyl glycinate | 20 |
| Cocoyl amido propyldimethyl glycine | 3 |
| Glycerine | 30 |
| Propylene glycol | 5 |
| Thickener | Appropriate amount |
| Citric acid | Appropriate amount |
| Preservative | Appropriate amount |
| Water | Balance |
| <Example 4-7> Paste cleanser | |
| | |
| Sodium N-acyl glycinate | 30 |
| Stearyldimethyl betaine | 8 |
| Glycerine | 30 |
| Propylene glycol | 5 |
| Polyethylene glycol | 1 |
| Citric acid | Appropriate amount |
| Water | Balance |

Preparation Method

The aforementioned ingredients are put into a pot and homogeneously mixed with a high speed mixer under heated conditions of 60° C.–80° C. After defoaming, filtration, and cooling, a weak acid skin cleanser is obtained.

Measurement of the Hardness Change Over Time

Samples from Comparative example 4-1 (0 wt % betaine-based ampholytic surfactant), Example 4-6 (1 wt % betaine-based ampholytic surfactant), Example 4-1 (2 wt % betaine-based ampholytic surfactant), Example 4-7 (3 wt % betaine-based ampholytic surfactant) were let stand in thermostatic baths at 25° C. and at 0° C. and the changes in the hardness was measured (immediately as well as one, two, three, and four weeks later). As for the method of measuring the hardness, a card tension meter (with a 200 g load and a 8 Φ sensing rod) was used to give a load which increased at a constant rate, and a needle with a constant area (8 Φ sensing rod) was pressed onto the sample. The point at which the pressure sensing rod stops still was defined as "hardness".

Results of the Measurement of the Hardness Change Over Time

FIG. 1 shows the hardness change over time of each sample. As clearly indicated in FIG. 1, Comparative example 4-1 (0 wt % cocoyl amido propyldimethyl glycine) showed an increase in the hardness over time at 0° C., but the increase in the hardness over time was suppressed by blending in cocoyl amido propyldimethyl glycine (Examples 4-1 and 4-6) Also at room temperature, Examples 4-1 and 4-6, which had cocoyl amido propyldimethyl glycine, showed suppressed increases in the hardness over time.

Evaluation Method and Evaluation Criteria for Sensation During Use

A panel of 18 healthy women (20–45 years old), after their skin was washed with water and dried, had 0.5 g of petrolatum homogeneously applied on their faces. Thirty minutes later, the skin cleansers of Examples and Comparative examples were used to wash their faces. Ease of squeezing out of the tube, rapid lathering, foaming, creamy foam, ease of rinsing, refreshing sensation during use and moist sensation after face washing were evaluated. For each evaluation, the top number of evaluation points was 100. Evaluation was based on the following criteria by using the average points of the 18 women. The results are shown in Table 7.

Ease of Squeezing Out of the Tube

⊚: Evaluation points of 75 or higher (Very soft and easy to squeeze out)

○: Evaluation points of 50–74 (Soft and easy to squeeze out)

Δ: Evaluation points of 25–49 (Somewhat hard and difficult to squeeze out)

X: Evaluation points of 25 or lower (Too hard to squeeze out at all)

[Rapid lathering]

⊚: Evaluation points of 75 or higher (Very rapid lathering)

○: Evaluation points of 50–74 (Rapid lathering)

Δ: Evaluation points of 25–49 (Somewhat slow lathering)

X: Evaluation points of 25 or lower (Slow lathering)

[Foaming]

⊚: Evaluation points of 75 or higher (Very good foaming)

○: Evaluation points of 50–74 (Good foaming)

Δ: Evaluation points of 25–49 (Somewhat poor foaming)

X: Evaluation points of 25 or lower (Poor foaming)

[Creamy Foam]

⊚: Evaluation points of 75 or higher (Very creamy)

○: Evaluation points of 50–74 (Creamy)

Δ: Evaluation points of 25–49 (Not very creamy)

X: Evaluation points of 25 or lower (Not creamy at all)

[Easy Rinsing]

⊚: Evaluation points of 75 or higher (Very easy to rinse)

○: Evaluation points of 50–74 (Easy to rinse)

Δ: Evaluation points of 25–49 (A little hard to rinse)

X: Evaluation points of 25 or lower (Fairly hard to rinse)

[Refreshing Sensation During Use]

⊚: Evaluation points of 75 or higher (Very refreshing)

○: Evaluation points of 50–74 (Refreshing)

Δ: Evaluation points of 25–49 (Some residue is sensed.)

X: Evaluation points of 25 or lower (Residue is sensed.)

[Moist Sensation After Face Washing]

⊚: Evaluation points of 75 or higher (Very moist)

○: Evaluation points of 50–74 (Moist)

Δ: Evaluation points of 25–49 (Not very moist)

X: Evaluation points of 25 or lower (Not moist at all)

TABLE 7

| Evaluation item | Example 4-1 | Comparative example 4-1 | Example 4-2 | Comparative example 4-2 | Example 4-3 | Comparative example 4-3 | Example 4-4 | Comparative example 4-4 |
| --- | --- | --- | --- | --- | --- | --- | --- | --- |
| Ease of squeezing out of a tube (0° C.) | ⊙ | X | ○ | X | ○ | X | ⊙ | X |
| Ease of squeezing out of a tube (25° C.) | ⊙ | ○ | ⊙ | Δ | ⊙ | ○ | ⊙ | ○ |
| Rapid lathering (0° C.) | ⊙ | ○ | ○ | X | ○ | X | ⊙ | ○ |
| Rapid lathering (25° C.) | ⊙ | ○ | ○ | X | ○ | X | ⊙ | ○ |
| Foaming (0° C.) | ⊙ | ⊙ | ○ | Δ | ○ | Δ | ⊙ | ⊙ |
| Foaming (25° C.) | ⊙ | ⊙ | ○ | Δ | ○ | Δ | ⊙ | ⊙ |
| Creamy foam (0° C.) | ⊙ | ⊙ | ○ | Δ | ○ | Δ | ⊙ | ⊙ |
| Creamy foam (25° C.) | ⊙ | ⊙ | ○ | Δ | ○ | Δ | ⊙ | ⊙ |
| Ease of rinsing (0° C.) | ⊙ | ⊙ | ⊙ | ⊙ | ⊙ | ⊙ | ⊙ | ⊙ |
| Ease of rinsing (25° C.) | ⊙ | ⊙ | ⊙ | ⊙ | ⊙ | ⊙ | ⊙ | ⊙ |
| Refreshing sensation (0° C.) | ⊙ | ⊙ | ⊙ | ⊙ | ⊙ | ⊙ | ⊙ | ⊙ |
| Refreshing sensation (25° C.) | ⊙ | ⊙ | ⊙ | ⊙ | ⊙ | ⊙ | ⊙ | ⊙ |
| Moist sensation after face washing (0° C.) | ⊙ | ⊙ | ⊙ | ⊙ | ⊙ | ⊙ | ⊙ | ⊙ |
| Moist sensation after face washing (25° C.) | ⊙ | ⊙ | ⊙ | ⊙ | ⊙ | ⊙ | ⊙ | ⊙ |

In Table 7, Comparative example 4-1, Comparative example 4-2, Comparative example 4-3, and Comparative example 4-4 all have a fatal problem in the ease of squeezing out of a tube at 0° C., but Example 4-1, Example 4-2, Example 4-3, and Example 4-4 do not have any problem and show improvement also in the ease of squeezing out of a tube and the rapid lathering properties at room temperature (25° C.). Furthermore, since each paste cleanser of Examples 4-1–4-4 is improved in terms of its hardness, the solubility in water improved, and so did rapid lathering properties and foaming.

These effects are confirmed in all the Examples which use an N-acyl amino acid salt. But Examples which use an N-acyl glycine salt (Example 4-1 and Example 4-4) are particularly superior in the ease of squeezing out of a tube at 0° C. and 25° C. and also have excellent effects in terms of rapid lathering, foaming, creaminess, ease of rinsing, refreshing sensation, and moist sensation after cleaning.

What is claimed is:

1. A method of suppressing hardening of an acidic skin cleanser consisting essentially of:
    an alkali salt of N-acylamino acid;
    an ampholytic surfactant;
    water; and
    an organic acid,
    said acidic skin cleanser having a pH of between 5–6.5,
    wherein said method comprises adding to said acidic skin cleanser said ampholytic surfactant, said ampholytic surfactant being selected from the group consisting of N-alkyl-N-carboxymethyl ammonium betaine, alkyldimethyl aminoacetic acid betaine, alkylimidazolinium betaine, cocoyl amido propyldimethyl glycine, coconut oil alkyl betaine, lauryl dimethyl amino-2-hydroxylpropyl sulfo betaine, lauric acid amide propyl betaine, and lauryl dimetyl amino propylsulfo betaine.

2. The method of claim 1, wherein said ampholytic surfactant is added to the acidic skin cleanser in the amount of 0.1–30 wt %.

3. The method of claim 1, wherein said ampholytic surfactant is added to the acidic skin cleanser in the amount of 0.5–15 wt %.

4. The method of claim 1, wherein said acidic skin cleanser in paste form is delivered to a user via a tube.

* * * * *